United States Patent
Epstein

(10) Patent No.: US 7,079,884 B1
(45) Date of Patent: Jul. 18, 2006

(54) BIOMEDICAL ELECTRODE HAVING A MATING CONFIGURATION AND ITS ASSOCIATED METHOD OF APPLICATION TO THE BODY

(76) Inventor: Stephen T. Epstein, 10 Lakeview Dr., Newtown, PA (US) 18940

( * ) Notice: Subject to any disclaimer, the term of this patent is extended or adjusted under 35 U.S.C. 154(b) by 46 days.

(21) Appl. No.: 10/739,369

(22) Filed: Dec. 19, 2003

(51) Int. Cl.
*A61B 5/04* (2006.01)

(52) U.S. Cl. .................. 600/391; 600/392; 600/393
(58) Field of Classification Search ........ 600/391–393; 607/149, 152
See application file for complete search history.

(56) References Cited

U.S. PATENT DOCUMENTS

| | | | |
|---|---|---|---|
| 3,998,215 A * | 12/1976 | Anderson et al. ........... 600/391 |
| 4,354,508 A * | 10/1982 | Murfitt et al. .............. 607/152 |
| 4,674,511 A * | 6/1987 | Cartmell ..................... 600/391 |
| 5,511,548 A | 4/1996 | Riazzi et al. ............... 128/641 |
| 6,134,480 A * | 10/2000 | Minogue .................... 607/152 |
| 6,532,379 B1 * | 3/2003 | Stratbucker ................. 600/391 |

* cited by examiner

*Primary Examiner*—Lee S. Cohen
(74) *Attorney, Agent, or Firm*—LaMorte & Associates

(57) ABSTRACT

An electrode system and the method of arranging the electrodes on the skin of a patient. The electrode system contains a plurality of electrode pads. At least some of the electrode pads have a convex side edge of a predetermined radius of curvature. At least some of the electrode pads have a concave side edge with the same predetermined radius of curvature. When applied to a patient's skin, two electrode pads are placed in adjacent abutment. The concave side edge of one electrode pad receives the convex side edge of the adjacent electrode pad. This produces a gapless adjoining connection between electrode pads that can be maintained throughout a wide range of orientations.

6 Claims, 3 Drawing Sheets

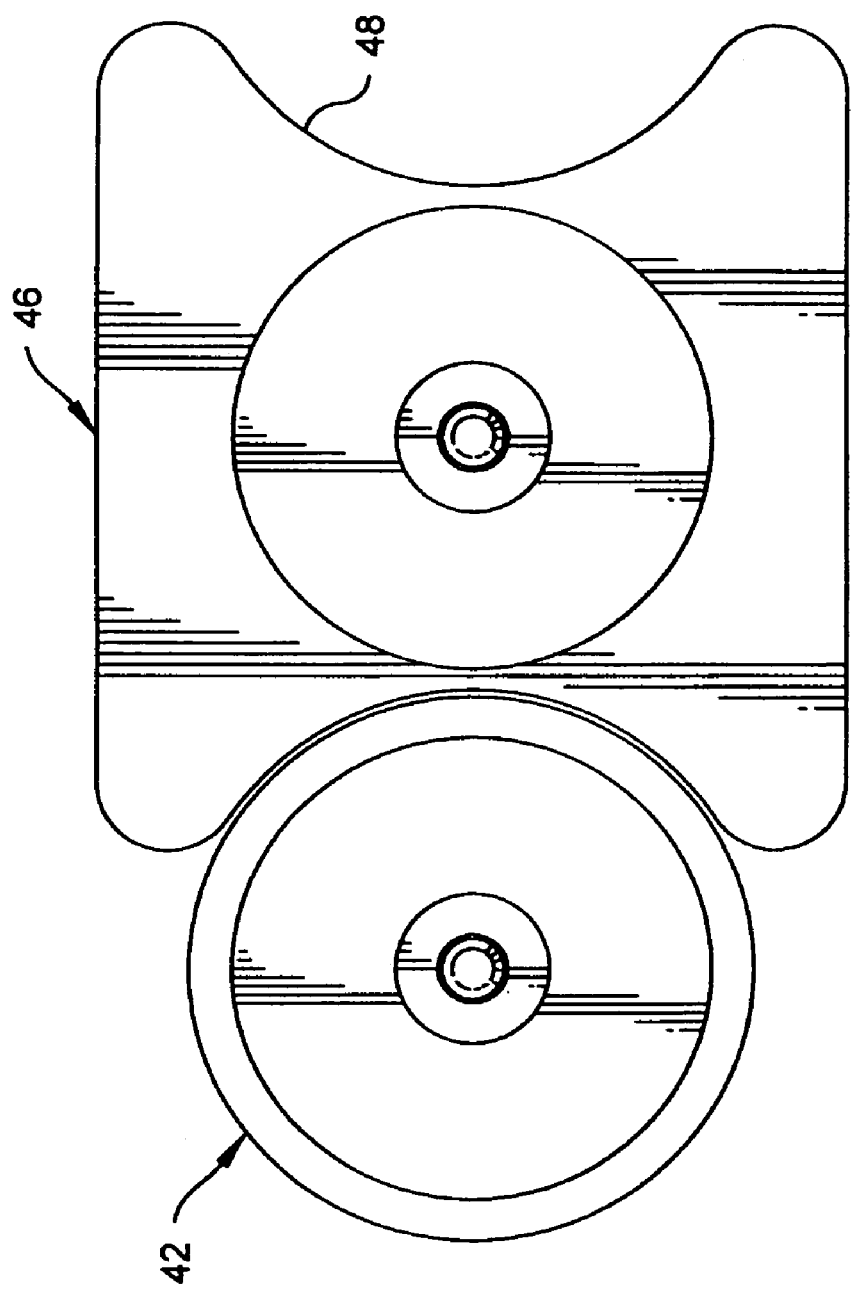

BIOMEDICAL ELECTRODE HAVING A MATING CONFIGURATION AND ITS ASSOCIATED METHOD OF APPLICATION TO THE BODY

BACKGROUND OF THE INVENTION

1. Field of the Invention

In general, the present invention relates to electrodes that are placed on the skin of a patient. More particularly, the present invention relates to the physical structure of such electrodes and the methods used to attach such electrodes to the skin.

2. Description of the Prior Art

There are many types of medical equipment that gather and process electrical signals generated from within a patient's body. For instance, an electrocardiogram instrument detects electrical nerve impulses generated by the heart. Those detected impulses are then converted into a graphical representation so that the heart's nerve impulses can be viewed and analyzed by a doctor. Many other pieces of medical equipment exist that detect electrical impulses from other organs of the body, such as the brain, lungs and uterus.

In order for a piece of medical equipment to detect an electrical impulse from within the human body, some type of electrical lead must be attached between the medical equipment and the body. The electrical lead must also mechanically attach to the body so that an electrical impulse generated within the body can be transmitted into the electrical lead and back to the medical equipment.

There are many types of electrical lead terminations that engage a patient's body and receive electrical impulses. Some of these prior art terminations are intrusive, in that they have an electrode lead that penetrates the skin or is introduced within an orifice of the body. However, for many types of medical testing, such as electrocardiograms, passive termination electrodes are used. A passive termination electrode is typically formed as a conductive pad. The conductive pad is glued, strapped or taped to the skin. The passive termination electrode detects electrical impulses through the skin without having to penetrate the skin. Such prior art passive termination electrodes are exemplified by U.S. Pat. No. 5,511,548 to Riazzi, entitled Biomedical Electrode Having A Secured One-Piece Conductive Terminal.

Passive termination electrodes that attach to the skin come in a wide assortment of sizes and configurations depending upon the intended application of the termination electrode. In many cases, the termination electrode is shaped to be round. This is done for two purposes. First, with a round termination electrode, the orientation of the termination electrode is irrelevant when it is placed on the skin. Second, a round termination electrode does not have salient points or corners that can chaff against clothing or folds in the skin, therein causing the termination electrode to peel away from the skin.

In many medical testing or monitoring procedures, multiple termination electrodes are attached to a patient's body. For instance, during an electrocardiogram, it is not uncommon for several termination electrodes to be attached to a patient's chest. The position of where the termination electrodes attach to the body are very specific. In order to obtain accurate data, each termination electrode must be attached to the body within a small, specific area of the body. However, when traditional round termination electrodes are used, the round shape of the termination electrodes prevents the termination electrodes from being attached to the body in close proximity without overlapping. Often a physician is required to custom cut termination electrodes so that the physician can place all the termination electrodes on the area of the body without overlapping. This is especially true with smaller patients, such as children, that have small body frames.

Furthermore, many medical testing and monitoring procedures, such as cardiac stress tests, require that a patient wear multiple termination electrodes as the patient exercises. Accordingly, there is a great deal of body movement during the test. When prior art electrode terminations are cut or are overlapped, there exist gaps and points that can cause discomfort to the patient as they move. Furthermore, the gaps and points tend to peel away from the skin as the patient moves, especially if the termination electrode is being contacted by clothing or a moving arm.

A need therefore exists for an improved passive termination electrode that enables multiple termination electrodes to be placed in a dense concentration on a small patch of skin without the termination electrodes overlapping or requiring cutting. A need also exists for a termination electrode that can be placed on the skin in dense concentrations without producing gaps or salient points that can cause the termination electrodes to prematurely detach. These needs are met by the present invention device as it is described and claimed below.

SUMMARY OF THE INVENTION

The present invention is a new electrode system and method of arranging the electrodes on the skin of a patient. The electrode system contains a plurality of electrode pads. At least some of the electrode pads have a convex side edge of a predetermined radius of curvature. At least some of the electrode pads have a concave side edge with the same predetermined radius of curvature. When applied to a patient's skin, the two electrode pads are placed in adjacent abutment. The concave side edge of one electrode pad receives the convex side edge of the adjacent electrode pad. This produces a gapless adjoining connection between electrode pads that can be maintained throughout a wide range of orientations.

Each electrode pad can have both a convex side edge and a concave side edge. Alternatively, different types of electrode pads can be provided, wherein a first type has at least one convex side edge and a second type has at least one concave side edge.

Each electrode pad is coupled to a terminal. The terminals enable each of the electrode pads to be connected to a separate lead that is extending from a piece of medical equipment.

BRIEF DESCRIPTION OF THE DRAWINGS

For a better understanding of the present invention, reference is made to the following description of exemplary embodiments thereof, considered in conjunction with the accompanying drawings, in which:

FIG. 3 is a top view of a plurality of termination electrodes in accordance with a second exemplary embodiment of the present invention.

DETAILED DESCRIPTION OF THE DRAWINGS

Figure 1:
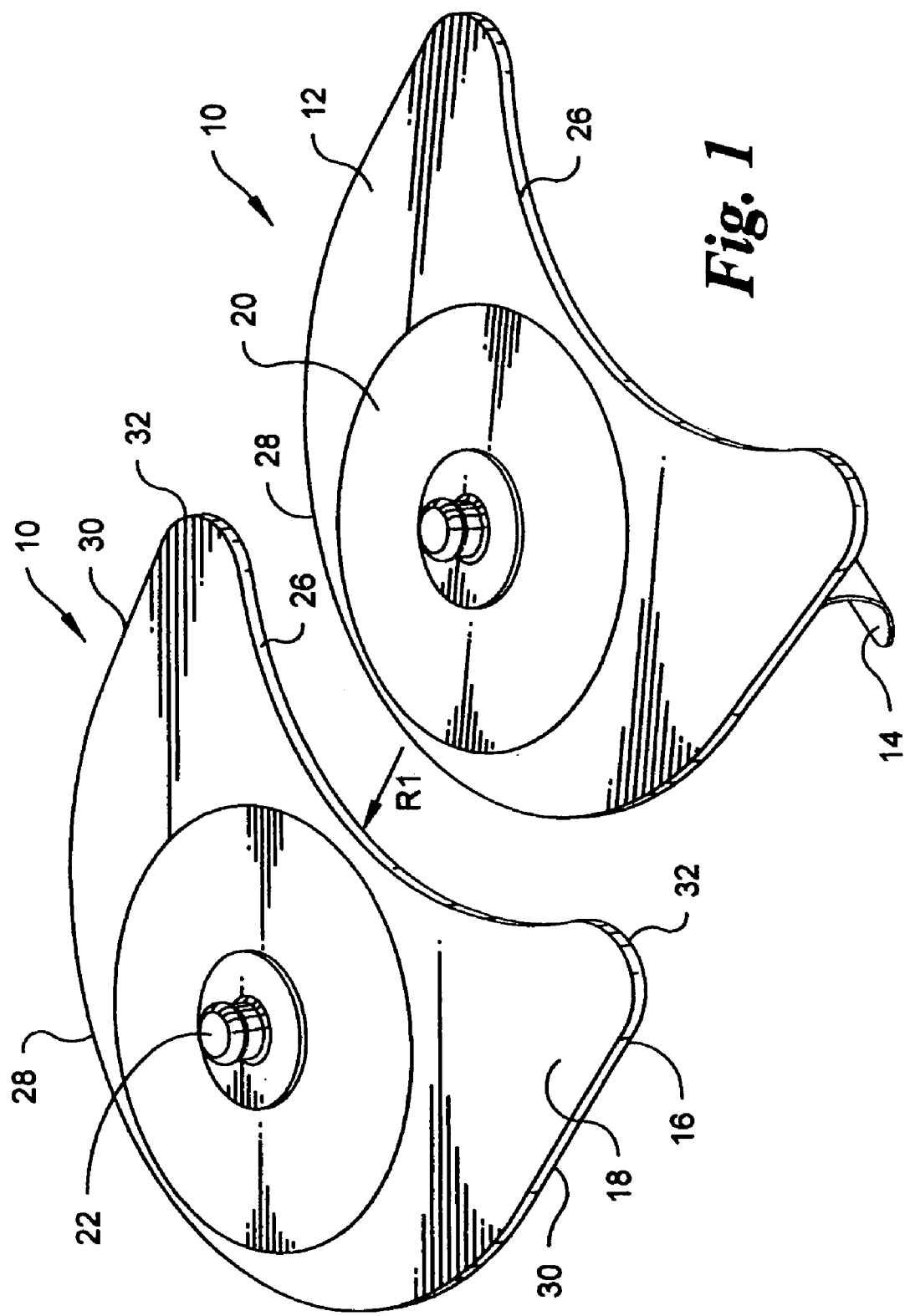
FIG. 1 is a perspective view of a first exemplary embodiment of two termination electrodes in accordance with the present invention.

Referring to FIG. 1, a first exemplary embodiment of two present invention termination electrodes 10 are shown. Each termination electrode 10 has an enlarged attachment base 12. Under the attachment base 12 is a smaller conductive pad that abuts against the skin of a patient. The attachment base 12 is preferably coated on its bottom surface 16 with adhesive. An optional protective covering 14 can be disposed over the bottom surface 16 of the attachment base 12. The protective covering 14 covers the adhesive prior to use. The protective covering 14 can be selectively peeled away and the bottom surface 16 of the attachment base 12 when the attachment base 12 is about to be applied to the skin of a patient.

On the top surface 18 of the attachment base 12 is located an insulated disc 20 of non-conductive material. A terminal 22 extends through the insulated disc 20 and interconnects to the conductive pad under the attachment base 12. Consequently, any electrical signal received by the attachment base 12 is detectable through the terminal 22. The terminal 22 connects to the lead of a piece of medical equipment (not shown).

One unique feature of the present invention termination electrode 10 is the shape of the attachment base 12. The attachment base 12 of the termination electrode 10 has a concave side surface 26 and a convex side surface 28. The concave side surface 26 has a radius of curvature R1. This radius of curvature R1 is also shared by the convex side surface 28. As such, it will be understood that the concave side surface 26 and the convex side surface 28 have the same radius of curvature R1.

The convex side surface 28 leads into two opposing straight side surfaces 30. The straight side surfaces 30 interconnect the top and bottom of the convex side surface 28 to the top and bottom of the concave side surface 26. The transition corners 32 between the straight side surfaces 30 and the concave side surface 26 are also curved, therein preventing the attachment base 12 from having sharp salient points.

Figure 2:
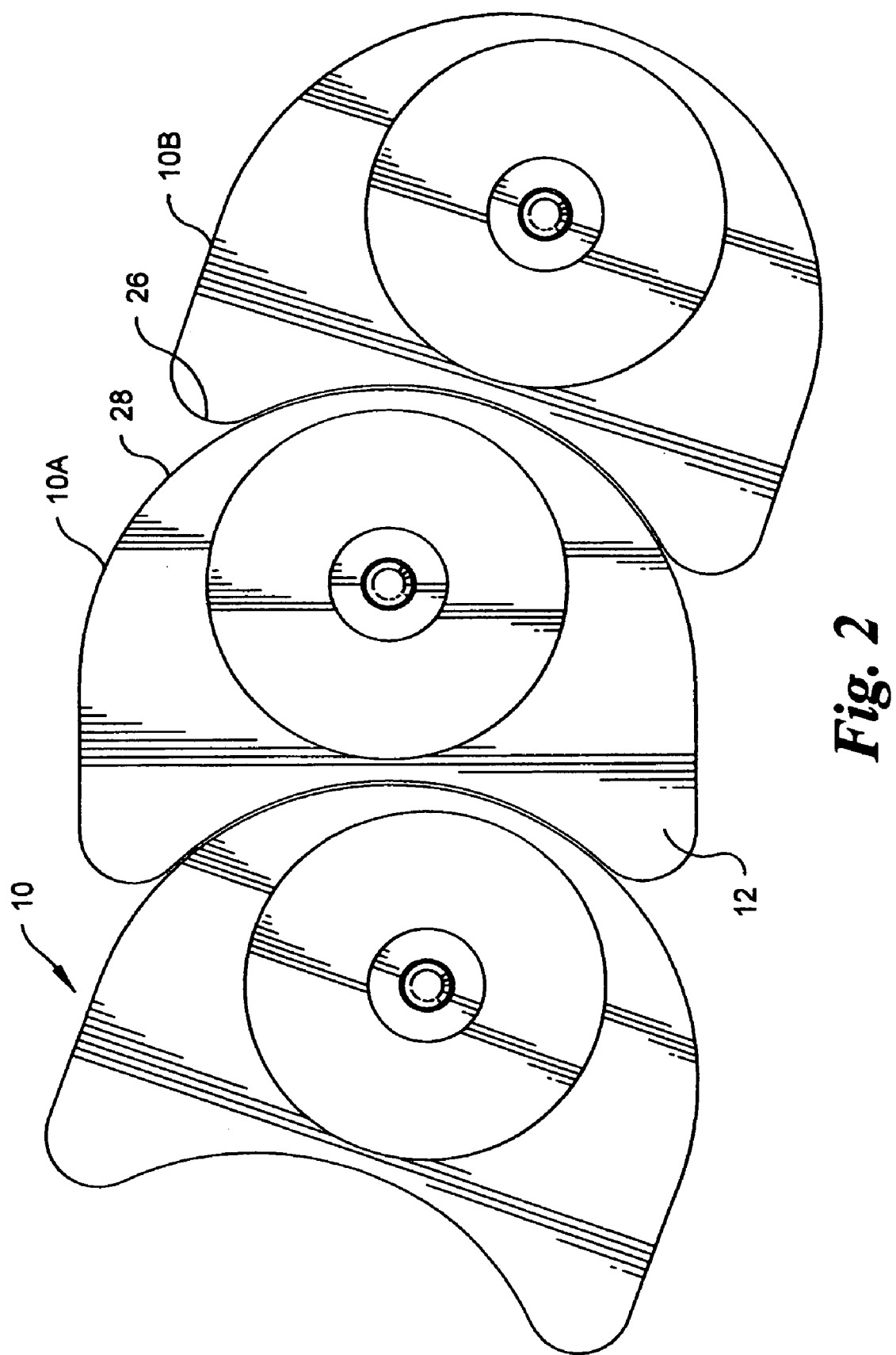
FIG. 2 is a top view of a plurality of termination electrodes of the type shown in FIG. 1, being interconnected in a common application.

Referring to FIG. 2, it can be seen that the convex side surface 28 of any attachment base 12 from one termination electrode 10A can intermesh with the concave side surface 26 of the attachment base 12 of an adjacent termination electrode 10B. Furthermore, the attachment base 12 of one termination electrode 10A can remain intermeshed with the attachment base 12 of an adjacent termination electrode 10B throughout a range of rotation of at least ninety degrees. Thus, multiple termination electrodes 10 can be interconnected even though each of the termination electrodes has an orientation that differs from that of the other termination electrodes.

As a consequence, multiple termination electrodes 10 can be attached to a patient in a dense pattern on just a small area of the patient's body. The termination electrodes 10 allow no open spaces between adjacent termination electrodes 10. As a result, there are no open edges between adjacent termination electrodes 10 that can catch on the body or clothes and cause a termination electrode to peel away from the skin. Furthermore, each termination electrode 10 can be attached to the body in an orientation different from that of the previous or subsequent termination electrode 10. Thus, a physician can apply the termination electrodes 10 to a patient's body in many different patterns without disrupting the inter-mating connection between adjacent termination electrodes 10.

Referring to FIG. 3., alternate embodiments of the present invention termination electrodes are provided. In the shown embodiment, there are two separate types of termination electrodes. The first termination electrode 42 is circular, and thus has convex sides 44. The second termination electrode 46 has two concave sides 48. Thus, the first type of termination electrode 42 will interconnect with the second type of termination electrode 46 along a continuous joint. Thus, no gap will exist between any of the first type of termination electrodes 42 that is joined to the second type of the termination electrodes 46. As a result, there are no open edges between adjacent termination electrodes 42, 46 that can catch on the body or clothes and cause either termination electrode 42, 46 for peel away from the skin.

The radius of curvature of the convex sides 44 on the first type of termination electrode 42 is the same as the radius of curvature of the concave sides 48 on the second type of termination electrode 46. As a result, the first type of termination electrode 42 can remain interconnected with the second type of termination electrode 46 throughout a large range of orientations. Furthermore, each of the termination electrodes 42, 46 can be attached to the body in an orientation different from that of the previous or subsequent termination electrode. Thus, a physician can apply the termination electrodes 42, 46 to a patient's body in many different patterns without disrupting the inter-mating connection between different types of termination electrodes 42, 46.

In the embodiment of FIG. 3, the second type of termination electrode 46 has two concave side. Such a configuration is merely exemplary and it will be understood that all four sides can be configured to be concave.

It will be understood that the embodiments of the present invention termination electrodes that are described and illustrated herein are merely exemplary and a person skilled in the art can make many variations to the embodiments shown without departing from the scope of the present invention. All such variations, modifications and alternate embodiments are intended to be included within the scope of the present invention as defined by the appended claims.

What is claimed is:

1. An electrode device for providing electrical contact with a person's skin, comprising:
   an attachment base having a first straight side edge, an opposite second straight side edge, a curved concave side edge extending between said first straight side edge and said second straight side edge and a curved convex side edge extending between said first straight side edge and said second straight side edge, wherein said first straight edge, said second straight edge, said curved concave side edge and said curved convex side edge define a complete periphery of said attachment base, and wherein said curved concave side edge and said curved convex side edge have a common radius of curvature; and
   a terminal extending upwardly from said attachment base that enables said electrode device to be individually connected to a test wire lead.

2. An electrode system for providing electrical contact with a person's skin, comprising:
   a plurality of electrode pads that are electrically isolated from one another, each of said electrode pads including:
   a terminal connection;
   a first straight side edge, an opposite second straight side edge, a curved concave side edge and a curved convex side edge, wherein said first straight edge, said second straight edge, said curved concave side edge and said curved convex side edge define a complete periphery of an electrode pad;

wherein said curved concave side edge and said curved convex side edge have a common radius of curvature; and wherein said concave side edge of a first said electrode pads receives said convex side edge of a second of said electrode pads creating a gapless seam between said first and said second of said electrode pads when said first and said second of said electrode pads are placed in adjacent abutment; and wherein said gapless seam is maintained throughout a relative range of motion of at least 90 degrees between said first and said second of said electrode pads.

3. The system according to claim 2, wherein each of said plurality of electrode pads have identical shapes.

4. The system according to claim 2, wherein each of said electrode pads includes a separate, independent terminal that extends upwardly therefrom.

5. A method of connecting electrodes to the human body, comprising the steps of:

providing a plurality of electrode pads, wherein, each of said electrode pads is identical and has a first straight side edge, an opposite second straight side edge, a curved concave side edge and a curved convex side edge, wherein said first straight edge, said second straight edge, said curved concave side edge and said curved convex side edge define a complete periphery of an electrode pad, and wherein said curved concave side edge and said curved convex side edge have a common radius of curvature;

attaching a first of said electrode pads to a patient's body;

attaching a second of said electrode pads to said patient's body immediately adjacent said first of said electrode pads within a range of relative orientations, wherein said concave side edge of said first of said electrode pads receives said convex side edge of a second of said electrode pads creating a gapless adjoining connection between said first and said second of said electrode pads throughout said relative range of orientations.

6. The method according to claim 5, further including the step of connecting each of said plurality of electrode pads to a separate test lead.

\* \* \* \* \*